US006407319B1

(12) United States Patent
Rose-Fricker et al.

(10) Patent No.: US 6,407,319 B1
(45) Date of Patent: Jun. 18, 2002

(54) KENTUCKY BLUEGRASS VARIETY KNOWN AS 'NORTH STAR'

(75) Inventors: Crystal Rose-Fricker, Canby, OR (US); William A. Meyer, Colts Neck, NJ (US)

(73) Assignee: Pure Seed Testing, Inc., Canby, OR (US)

( * ) Notice: Subject to any disclaimer, the term of this patent is extended or adjusted under 35 U.S.C. 154(b) by 37 days.

(21) Appl. No.: 09/589,529

(22) Filed: Jun. 7, 2000

(51) Int. Cl.[7] .................................................. A01H 5/00
(52) U.S. Cl. ........................................ 800/320; 800/260
(58) Field of Search ................................. 800/320, 260; Plt./393

(56) References Cited

FOREIGN PATENT DOCUMENTS

| WO | WO 92/04449 | 3/1992 |
| WO | WO 92/11764 | 7/1992 |

OTHER PUBLICATIONS

Harrington et al., "Tolerance to Herbicides of Ground Cover Species for New Zealand Orchards," *Plant Protection Quarterly* 13:111–116 (1998).

Comes et al., "Differential Response to Glyphosate and Growth Patterns of Red Fescue *Festuca–Rubra*," *J. Aquatic Plant Management* 23:32–35 (1985) (abstract).

Turf–Seed, Inc., Pure Seed Testing, Inc., *Field Day 18*, Jun. 15, 2000, pp. 1–148.

Turf–Seed, Inc., Pure Seed Testing, Inc., *Field Day 17*, Jun. 15, 1999, Front cover and p. 12.

Turf–Seed, Inc., Pure Seed Testing, Inc., *Field Day 14*, Jun. 20, 1996, Front cover and p. 32.

Declaration from Crystal Rose–Fricker executed on Oct. 16, 2000.

Turf–Seed, Inc., Pure Seed Testing, Inc., *Field Day '91*, Front cover and p. 45.

*Primary Examiner*—Bruce R. Campbell
(74) *Attorney, Agent, or Firm*—Klarquist Sparkman, LLP

(57) ABSTRACT

A Kentucky bluegrass variety known as 'North Star' (experimental code PST-A7-60), and seed used to produce the grass are provided. Methods of using the grass plant and the seed are also provided. This grass is particularly suitable for use in lawns, golf courses, sod, and other turfs where excellent turf quality is desired.

33 Claims, No Drawings

KENTUCKY BLUEGRASS VARIETY KNOWN AS 'NORTH STAR'

BACKGROUND OF THE INVENTION

Kentucky bluegrass (*Poa pratensis* L.) is a short- to medium height, cool-season, perennial grass that has smooth, soft, green to dark green leaves with boat-shaped tips. It grows best during cool, moist weather on well-drained, fertile soils with a pH between 6 and 7 and spreads via rhizomes to form a dense sod. Historically, Kentucky bluegrass has been important for use in agriculture in the North Central and Northeastern regions of the United States. This is because Kentucky bluegrass tolerates close and frequent grazing or mowing better than other cool-season grasses. This ability makes Kentucky bluegrass and ideal species in permanent pastures, as well as in turf situations (e.g., lawns, parks, sod production, and athletic fields).

More recently, Kentucky bluegrass has become an important turf grass in part because its rhizomes form a dense sod, which also makes it ideal for erosion control, particularly in grass waterways.

SUMMARY OF THE INVENTION

The inventor has produced a Kentucky bluegrass variety termed 'North Star' (experimental code PST-A7-60) that is different from all known varieties of Kentucky bluegrass. Particularly, PST-A7-60 has an early heading date, short mature plant height (i.e., from about 19 cm to about 36 cm), high flag leaf height (i.e., from about 6 cm to about 15 cm), and a long panicle length (i.e., from about 3 cm to about 10 cm).

At least 2500 seeds of PST-A7-60 have been deposited with the ATCC. Therefore, these seeds are known and readily available to the public.

In one embodiment, the invention provides Kentucky bluegrass plants having the morphological and physiological characteristics of PST-A7-60, as well as seeds of such plants. In another embodiment, the invention provides grass plants having the genotype of PST-A7-60. The invention also encompasses Kentucky bluegrass plants that are produced by crossing PST-A7-60 with other grass varieties, as well as seeds of such plants. In another aspect, the invention provides a method of producing grass seed, comprising planting seed from PST-A7-60 under conditions that result in the germination of the seed, growth of grass plants and setting of progeny seed, and then harvesting the progeny seed.

These and other aspects of the invention will become more apparent from the following description.

DESCRIPTION OF THE INVENTION

Seed Deposits, Description of Plants

Seeds of the Kentucky bluegrass variety termed 'North Star' (experimental code PST-A7-60) were deposited with the American Type Culture Collection (ATCC, Manassas, Va.) on May 26, 2000, under accession number PTA-1969. The variety is also maintained at, and available from, Pure Seed Testing, Inc., P.O Box 449, Hubbard, Oreg. 97032.

The following growth characteristics were observed for PST-A7-60 plants that were grown in seeded rows near Hubbard, Oreg. or in Adelphia, N.J. Variations on these measurements may be observed for plants of differing ages, grown in other locations and/or under different prevailing weather conditions.

Additionally, the information provided below relating to turf quality ratings (seasonal density, genetic color, and leaf texture) and disease/environmental resistance (stripe rust, leaf spot, and traffic tolerance) is derived from various turf trials. These data are expressed in numbers ranging from 1–9, with I representing low turf quality, low disease resistance, or low environmental resistance, and 9 representing desirable high turf quality, no disease, or no environmental damage.

TABLE 1

1997 calendar day measurements taken on one Kentucky bluegrass seed yield trial seeded fall of 1997 and one Plant Variety Protection (P.V.P.) spaced plant trial planted fall of 1995 both near Hubbard, Oregon

| ENTRY | 1997 S.Y.T. | 1995 P.V.P Trial |
|---|---|---|
| 'North Star' (PST-A7-60) | 119.5 | 117 |
| 'Merit' | 127.5 | 125.25 |
| 'Nugget' | 121.5 | 115 |
| L.S.D. (0.05)* | 6.08 | 2.6272 |

*To determine statistical differences among entries, subtract one entry's mean from another entry's mean. Statistical differences occur when this value is equal to or larger than the corresponding L.S.D. value.

TABLE 2

1998 mean morphological measurements taken on a Kentucky bluegrass seed yield trial seeded fall of 1997 near Hubbard, Oregon

| ENTRY | PLANT HEIGHT (cm) | FLAG LEAF HEIGHT (mm) | PANICLE LENGTH (mm) |
|---|---|---|---|
| 'North Star' (PST-A7-60) | 35.85 | 12.59 | 6.91 |
| 'Nugget' | 29.93 | 9.08 | 5.63 |
| L.S.D. (0.05) | 2.42 | 1.91 | 0.51 |

TABLE 3

1996, 1997 and 1999 mean morphological measurements taken on two Kentucky bluegrass spaced plant nurseries planted fall of 1995 and 1997 near Hubbard, Oregon

| | 1995 TRIAL | | | 1997 TRIAL | | |
|---|---|---|---|---|---|---|
| | 1996 | 1997 | 1997 | 1999 | | |
| ENTRY | PLANT HEIGHT (cm) | PLANT HEIGHT (cm) | PANICLE LENGTH (cm) | PLANT HEIGHT (cm) | FLAG LEAF HEIGHT (cm) | PANICLE LENGTH (cm) |
| 'North Star' | 35.817 | 42.1 | 6.7 | 24.6 | 10.1 | 6.3 |
| 'Nugget' | 42.833 | 37.4 | 7.5 | 13.4 | 6.0 | 5.0 |
| 'Merit' | 55.033 | 46.5 | 8.4 | NIT* | NIT* | NIT* |
| 'Apex' | NIT* | NIT* | NIT* | 25.3 | 11.6 | 5.7 |
| L.S.D. (0.05) | 3.25 | 2.9 | 0.6 | 2.3 | 1.6 | 0.7 |

TABLE 4

Performance of Kentucky bluegrass cultivars and selections in a turf trial seeded in September 1995 at Adelphia, New Jersey

| ENTRY | TURF QUALITY 1996 Avg 9 = best | TURF COLOR Nov. 1995 9 = darkest color |
|---|---|---|
| 'North Star' (PST-A7-60) | 5.9 | 6.7 |
| 'Nugget' | 4.5 | 4.3 |
| L.S.D. (0.05) | 0.8 | 1.2 |

NIT* = Not in Trial

TABLE 5

Kentucky bluegrass turf trial seeded fall of 1994 near Hubbard, Oregon

| ENTRY | 1995 Mean T.Q.* 9 = best | 1995–1997 Mean T.Q. 9 = best | 1995 Stripe Rust 9 = no disease | 1995 Leaf Spot 9 = no disease | 1997 Traffic Tolerance Data 9 = no traffic damage |
|---|---|---|---|---|---|
| 'North Star' | 6.8 | 5.7 | 7.3 | 6.0 | 6.0 |
| 'Nugget' | 5.1 | 4.8 | 5.7 | 4.7 | 2.7 |
| L.S.D. (0.05) | 1.0 | 0.8 | 1.4 | 1.4 | 1.9963 |

T.Q.* = Turf Quality rating

TABLE 6

1999 Salt Screening. Kentucky bluegrass sprigged from 1995 National Turf Trial. Screened at ca. 10 ppt salinity for eight weeks (March 24–May 25, 1999)

| Entry | Salt Damage |
|---|---|
| North Star | 1.24 |
| Ascot | 1.45 |
| Moonlight | 1.90 |
| Limousine | 1.96 |
| Wildwood | 1.99 |
| Blacksburg | 2.33 |
| Midnight | 2.34 |
| Baron | 2.45 |
| Brilliant | 2.60 |
| America | 2.70 |
| Blackstone | 2.70 |
| Unique | 2.78 |
| Glade | 2.92 |
| Challenger | 2.95 |
| Kenblue | 3.20 |
| Haga | 3.27 |
| L.S.D. | 0.38 |

0 = No Damage
1 = 1–25% Damage
2 = 25.1–50% Damage
3 = 50.1–75% Damage
4 = 75.1–99.9% Damage
5 = Dead The 'North Star' variety is additionally characterized by the following results from various trials.

The mean turf quality ratings for 'North Star' in a Kentucky bluegrass turf trial that was seeded in the fall of 1995 near Rolesville, N.C., were 5.5 in 1996 and 6.1 in 1997 (9=best).

The mean summer turf quality ratings for 'North Star' in a Kentucky bluegrass turf trial that was seeded in the fall of 1995 near Rolesville, N.C. were 5.8 in 1996 and 5.8 in 1997.

The mean leaf spot rating for 'North Star' in a Kentucky bluegrass turf trial that was seeded in the fall of 1997 and maintained at 2.5" near Rolesville, N.C. was 8.0 in 1998 (9=no disease).

The mean winter color ratings for 'North Star' in a Kentucky bluegrass turf trial that was seeded in the fall of 1995 near Rolesville, N.C. was 4.7 in 1996 and 6.7 in 1997 (9=dark green).

The mean stem rust and turf quality ratings for 'North Star' in a low maintenance Kentucky bluegrass turf trial that was seeded in the fall of 1995 near Hubbard, Oreg. were 7.0 for stem rust, 6.0 for turf quality in 1996, and 5.8 for turf quality in 1997 (9=no disease; best quality).

The mean leaf spot quality ratings for 'North Star' in the National Turf Evaluation Program (NTEP) Kentucky bluegrass trial that was seeded in 1995 and grown under medium/high input conditions was 6.9 in 1997 (9=no disease).

The mean turf quality ratings for 'North Star' in a low mow (0.5") Kentucky bluegrass turf trial seeded in the fall of 1996 near Hubbard, Oreg. were 6.2 in 1997 and 5.9 in 1998 (9=best).

The melting-out (spring) rating for 'North Star' in the NTEP Kentucky bluegrass trial that was seeded in 1995 and grown under medium/high input was 9.0 in 1997 (9=no damage).

The mean turf grass quality rating for 'North Star' in the NTEP Kentucky bluegrass trial that was seeded in 1995 and grown under medium/high input conditions at twenty-eight locations (full sun) in the U.S. and Canada was 6.2 in 1997 (9=best).

The mean turf grass quality rating for 'North Star' in the NTEP Kentucky bluegrass trial that was seeded in 1995 and grown under low input conditions at nineteen locations in the U.S. and Canada was 5.4 in 1997 (9=best).

The mean summer density ratings for 'North Star' in the NTEP Kentucky bluegrass trial that was seeded in 1995 and grown under low input conditions was 6.7 in 1997 (9=maximum density).

The mean genetic color ratings for 'North Star' in the NTEP Kentucky bluegrass trial seeded in 1995 and grown under low input conditions was 6.8 in 1997 (9=dark green).

The mean genetic color quality ratings for 'North Star' in the NTEP Kentucky bluegrass trial seeded in 1995 and grown under medium/high input conditions was 7.0 in 1997 (9=dark green).

The mean fall density ratings for 'North Star' in the NTEP Kentucky bluegrass trial seeded in 1995 and under low input conditions was 7.2 in 1997 (9=maximum density).

The mean leaf texture ratings for 'North Star' in the NTEP Kentucky bluegrass trial seeded in 1995 and grown under medium/high input conditions was 6.6 in 1997 (9=very fine).

The mean percent living ground cover (summer) ratings for 'North Star' in a Kentucky bluegrass trial seeded in 1995 and grown under low input conditions was 75.3 in 1997.

The mean summer density ratings for 'North Star' in the NTEP Kentucky bluegrass trial seeded in 1995 and grown under medium/high input conditions was 7.1 in 1997 (9=maximum density).

Breeding History of the Kentucky Bluegrass Variety 'North Star' (PST-A7-60)

'North Star' Kentucky bluegrass (*Poa pratensis L.*) was developed by Pure Seed Testing, Inc. 'North Star' originated as a single apomictic plant selected from the progeny of the cross 'Merit' Kentucky bluegrass X 'Eagleton 1425' Kentucky bluegrass.

Plants of 'Merit' and 'Eagleton 1425' were removed from space plant fields early spring at Pure Seed Testing, Inc., near Hubbard, Oreg., in 1986 and moved to a greenhouse. Day length was extended through artificial lighting to promote flowering. 'Merit' was mass pollinated with 'Eagleton' in a crossing box. Seedlings from this cross were established in a field nursery at Pure Seed Testing in Oregon fall of 1986.

During the summer of 1987, PST-A7-60 was identified as a promising hybrid. Seed from the PST-A7-60 plant was harvested and used to establish 100 plants that were planted in a field nursery fall of 1988 to determine the apomixis level.

The summer of 1989, it was determined that PST-A7-60 is a facultative apomict with approximately 95% of its progeny appearing genetically identical to the maternal parent.

Seed harvested in 1989 was used to establish turf trials in Oregon and at Rutgers University. The 'North Star' variety was subsequently evaluated in turf and seed yield trials. The fall of 1994, PST-A7-60 was vegetatively sprigged from the 1989 turf trials in Adelpia, N.J. at Rutgers University and increased to a 990 spaced plant nursery in Oregon at Pure Seed Testing. In the summer of 1995, this nursery was rogued removing all aberrant, off-type plants. Eight hundred and forty-nine plants were harvested as the breeder seed of 'North Star' Kentucky bluegrass.

Breeder seed is maintained at Pure Seed Testing in Oregon.

Seed propagation is limited to three generations of increase from breeder seed—one each of foundation, registered, and certified.

'North Star' is a stable and uniform variety. No off-type plants or variants have been observed in the reproduction or multiplication of 'North Star'. 'North Star' has produced turf of good quality and uniformity.

Production of the 'North Star' (PST-A7-60) Variety

PST-A7-60 Kentucky bluegrass can be grown under normal conditions for growing turf grasses, and bulk seed for large-scale planting can be obtained by methods known in certified seed production. For example, bulk seed may be produced by planting PST-A7-60 seeds obtained from either ATCC or Pure Seed Testing, Inc., allowing the mature plants to produce seed by apomixis or cross-pollination with each other and then collecting the seed. Standard precautions should be taken to prevent cross-pollination from other grasses, such as growing the variety in an isolated plot of sterilized soil, removing adjacent vegetation, etc. The PST-A7-60 seeds deposited with ATCC are breeder seeds; propagation of plants from these seeds should preferably be performed under the conditions specified in the 1998 Oregon Certified Seed Handbook, published by Oregon State University Extension Service, Corvallis, Oreg. 97331.

The 'North Star' variety can also be asexually repoduced via propagules. Vegetative propagules: As used herein, the term vegetative propagules means sprigs, plugs, stolons and sod.

Exemplary Uses of Kentucky Bluegrass Variety 'North Star' (PST-A7-60)

The Kentucky bluegrass PST-A7-60 is useful for planting in a variety of different environments. For example, the Kentucky bluegrass variety is useful for planting on steep slopes where soil erosion is likely to occur.

The Kentucky bluegrass PST-A7-60 is also useful in part because of its overall disease resistance, salt tolerance, tolerance to low mowing (i.e. at 0.5") and its high turf rating. These features render especially useful for sod production, athletic fields, golf course fairways, golf course roughs, parks, home lawns, and for mixing with other varieties of Kentucky bluegrass seed. 'North Star' can also be used in blends with perennial ryegrass, tall fescue or fine fescue varieties. Thus, the 'North Star' variety (PST-A7-60) is especially marketable and therefore useful.

Northstar's salt tolerance makes it useful in areas where effluent water is used for irrigation and areas along ocean sides where other turf grasses may not survive due to ocean spray.

Molecular Characterization of the Kentucky Bluegrass Variety 'North Star'

Proteins from the 'Northstar' (PST-A7-60), 'Merit', and 'Apex' Kentucky bluegrass varieties were tested to identify and compare various banding patterns.

Total protein banding patterns were visualized on two different isoelectric focusing gels. The first gel was at pH 3–7 and the second gel was at pH 3–10. The total protein-banding pattern was then visualized via silver staining.

The banding patterns of phosphoglucomutase (PGH), superoxidedismutase (SOD), esterase (EST), phospohexose isomerase (PHI), and peroxidase (PER) were visualized on two different isoelectric focusing gels. The esterase and peroxidase enzymes were run on gels at pH 3–10, and the phosphoglucomutase (PGM), superoxidedismutase (SOD), and phosphohexose isomerase were run on gels at pH 3–7.

1. Results

'North Star' and 'Apex' had different PHI banding profiles than 'Merit'. 'North Star' and 'Merit' had different EST banding profiles than 'Apex'. 'North Star' and 'Apex' had different PER profiles than 'Merit'. 'Merit' and 'North Star' had different PGM/SOD banding profiles than 'Apex'.

The results are summarized in Table 7, below. A letter was assigned to each banding pattern that was different.

The electrophoretic analysis was conducted by HyPure® (part of Perkin Elmer Life Sciences), 3985 Eastern Road, Norton, Ohio 44203, U.S.A.

TABLE 7

Compilation of Results from Protein Analysis

| Variety Name | PHI (HyPure Gel FS-5080) | EST (HyPure Gel FS-5480) | PER (HyPure Gel FS-5480) | PGM/SOD (HyPure Gel FS-5080) |
|---|---|---|---|---|
| SET 1 | | | | |
| 'NORTHSTAR' (PST-A7-60) | A | A | A | A |
| 'MERIT' | B | A | B | A |
| 'APEX' | A | B | A | B |

*A different letter was designated for each different banding pattern that was observed.

2. Methods

Five bulk samples were prepared for each type of test. The samples were prepared by grinding the seeds in a coffee grinder and then weighing out 200 mg×5 for each test. For the enzyme assays 500–700 μL of a glycine extraction solution was used per 200 mg crushed seed. The samples were incubated overnight at 4–8° C. and were then centrifuged the next morning. The resulting supernatant was then ready for running out on the isoelectric focusing gels.

The isoelectric focusing gels ran for 80 minutes and were then immediately placed into their corresponding stains. When the electrophoresis banding patterns reached desired intensity the reaction was stopped and the gels were washed in water. The gels were then air dried and ready for the interpretation.

Introducing Traits of Kentucky Bluegrass Variety 'North Star' Into Other Grass Varieties The morphological and physiological characteristics of the 'North Star' variety of Kentucky bluegrass may be introduced into other grass varieties by conventional breeding techniques. For example, the 'North Star' variety may be grown in pollination proximity to another variety of Kentucky bluegrass, allowing cross-pollination to occur between the 'North Star' variety and the other variety, and then harvesting the hybrid seeds. Plants grown from these hybrid seeds can then be tested for the maintenance of the molecular characteristics described above for the 'North Star' variety, and/or the plants can simply be observed to see if they display the same growth characteristics described in the above tables.

In certain embodiments, the present invention contemplates the transformation of cells derived from the 'North Star' variety with more than one advantageous transgene. Transgenes that confer resistance to herbicides, insect, disease (viral, bacterial, fungal, nematode) or drought resistance, standability, prolificacy, salt damage resistance, and quality are particularly useful. Examples of such genes and methods of transforming plants are described in U.S. Pat. No. 6,025,545 to Lundquist, et al., which is herein incorporated by reference.

Having illustrated and described the principles of the invention in multiple embodiments and examples, it should be apparent to those skilled in the art that the invention can be modified in arrangement and detail without departing from such principles. The invention, therefore, encompasses all modifications coming within the spirit and scope of the following claims.

What is claimed is:

1. A Kentucky bluegrass plant, comprising the morphological and physiological properties of a grass plant grown from the seed deposited under American Type Culture Collection (ATCC) No. PTA-1969.

2. Sod, comprising the grass plant of claim 1.

3. A golf course fairway, comprising the grass plant of claim 1.

4. The grass plant of claim 1 planted in a golf course tough.

5. The grass plant of claim 1 planted in a lawn.

6. The grass plant of claim 1 planted in an athletic field.

7. The grass plant of claim 1 planted in a park.

8. Progeny of a grass plant according to claim 1.

9. Seed of the grass plant of claim 1.

10. A seed mixture, comprising the seed of claim 9.

11. A vegetative sprig or clone of the grass plant of claim 1.

12. The grass plant of claim 1, further comprising at least one transgene.

13. Seed resulting from crossing the grass plant of claim 1 with a second grass plant.

14. A grass plant grown from the seed of claim 13.

15. Sod, comprising the grass plant of claim 14.

16. The grass plant of claim 14 planted in a golf course fairway.

17. The grass plant of claim 14 planted in a golf course rough.

18. The grass plant of claim 14 planted in a lawn.

19. The grass plant of claim 14 planted in an athletic field.

20. The grass plant of claim 14 planted in a park.

21. A method of producing grass seed, comprising
   (a) planting grass seed according to claim 9 under conditions that result in the germination of the seed, growth of grass plants and setting of progeny seed; and
   (b) harvesting the progeny seed.

22. Grass seed produced by the method of claim 21.

23. A mixture of grass seed comprising the grass seed of claim 22.

24. A method of producing a grass plant, the method comprising:
   (a) crossing a first grass plant with at least one other grass plant to produce at least one seed, wherein the first grass plant is a grass plant according to claim 1;
   (b) harvesting the seed; and
   (c) germinating the seed to produce at least one progeny grass plant.

25. A grass plant produced by the method of claim 24.

26. Sod, comprising the grass plant of claim 25.

27. The grass plant of claim 25 planted in a golf course fairway.

28. The grass plant of claim 25 planted in a golf course rough.

29. The grass plant of claim 25 planted in a lawn.

30. The grass plant of claim 25 planted in an athletic field.

31. The grass plant of claim 25 planted in a park.

32. A vegetative sprig or clone of the grass plant of claim 25.

33. The grass plant of claim 25, further comprising at least one transgene.

* * * * *

UNITED STATES PATENT AND TRADEMARK OFFICE
CERTIFICATE OF CORRECTION

PATENT NO.    : 6,407,319 B1
DATED         : June 18, 2002
INVENTOR(S)   : Rose-Fricker et al.

It is certified that error appears in the above-identified patent and that said Letters Patent is hereby corrected as shown below:

<u>Column 8,</u>
Line 29, "golf course tough" should read -- golf course rough --.

Signed and Sealed this

Fourteenth Day of January, 2003

JAMES E. ROGAN
*Director of the United States Patent and Trademark Office*